US006302331B1

(12) United States Patent
Dvorsky et al.

(10) Patent No.: US 6,302,331 B1

(45) Date of Patent: Oct. 16, 2001

(54) DIRECTIONALLY CONTROLLED EHD AEROSOL SPRAYER

(75) Inventors: James E. Dvorsky, Norwich Township; Songsdhit Chongsiriwatana, Columbus, both of OH (US)

(73) Assignee: Battelle Pulmonary Therapeutics, Inc., Columbus, OH (US)

( * ) Notice: Subject to any disclaimer, the term of this patent is extended or adjusted under 35 U.S.C. 154(b) by 0 days.

(21) Appl. No.: 09/552,970

(22) Filed: Apr. 20, 2000

Related U.S. Application Data

(60) Provisional application No. 60/130,893, filed on Apr. 23, 1999.

(51) Int. Cl.$^7$ .................. A01G 23/10

(52) U.S. Cl. .................. 239/3; 239/690.1; 239/692; 239/706

(58) Field of Search .................. 239/690, 690.1, 239/692, 695, 706, 708, 705, 696, 3; 361/227, 228; 128/200.14, 203.13, 204.13, 204.21

(56) References Cited

U.S. PATENT DOCUMENTS

| | | | | |
|---|---|---|---|---|
| 3,393,662 | | 7/1968 | Blackwell . | |
| 3,579,245 | | 5/1971 | Berry . | |
| 4,581,675 | * | 4/1986 | Kelly | 361/228 |
| 4,726,521 | | 2/1988 | Simm et al. . | |
| 4,749,125 | | 6/1988 | Escallon et al. . | |
| 4,830,872 | | 5/1989 | Grenfell . | |
| 4,989,793 | | 2/1991 | Gimple . | |
| 5,086,973 | | 2/1992 | Escallon et al. . | |
| 5,154,358 | | 10/1992 | Hartle . | |
| 5,290,600 | | 3/1994 | Ord et al. . | |
| 5,332,154 | | 7/1994 | Maier et al. . | |
| 5,400,975 | * | 3/1995 | Inculet et al. | 239/690.1 |
| 5,788,166 | * | 8/1998 | Valaskovic et al. | 239/708 |
| 5,813,614 | * | 9/1998 | Coffe | 239/690 |
| 6,105,877 | * | 8/2000 | Coffe | 239/690 |

FOREIGN PATENT DOCUMENTS

| | | | |
|---|---|---|---|
| 1071937 | | 2/1980 | (CA) . |
| 1569707 | | 6/1980 | (GB) . |
| 2327895-A | * | 2/1999 | (GB) . |
| 2334461-A | * | 8/1999 | (GB) . |
| 1010-323 | | 6/1981 | (SU) . |

* cited by examiner

*Primary Examiner*—David A. Scherbel
*Assistant Examiner*—Dinh Q. Nguyen
(74) *Attorney, Agent, or Firm*—Barry S. Bissell

(57) ABSTRACT

The invention provides an aerosol delivery method and system for producing a charged electrohydrodynamic (EHD) aerosol, discharging the aerosol and moving the discharged aerosol in a desired direction without substantial wetting of the device. The delivery system may include a spray nozzle for dispensing the fluid to be aerosolized and negatively charging the aerosol droplets, a discharge electrode generally downstream of the spray nozzle for generating a positive ion stream which intercepts and electrically neutralizes the negative aerosol droplets while also imparting a desired movement on the aerosol in a direction generally away from the discharge electrode and a reference electrode between the spray nozzle and the discharge electrode for modifying the electric field between the spray nozzle and the discharge electrode.

39 Claims, 6 Drawing Sheets

DIRECTIONALLY CONTROLLED EHD AEROSOL SPRAYER

RELATED APPLICATION

This application claims priority from U.S. Provisional Application 60/130,893 filed Apr. 23, 1999.

BACKGROUND OF THE INVENTION

1. Field of the Invention

This invention relates to devices and methods for controlling the delivery and the delivery direction of an aerosol, and particularly to a method and apparatus for induced aerosol flow in an electrohydrodynamic (EHD) sprayer.

2. Background

The use of electrohydrodynamic (EHD) apparatus to produce aerosols is well known. Recently, we have recognized that EHD devices are extremely useful to produce and deliver aerosols of therapeutic products.

In typical EHE) devices fluid delivery means deliver fluid to be aerosolized to a nozzle maintained at high electric potential. One type of nozzle used in EHD devices is a capillary tube that is capable of conducting electricity. An electric potential is placed on the capillary tube which charges the fluid contents such that as the fluid emerges from the tip or end of the capillary tube a so-called Taylor cone is formed. This cone shape results from a balance of the forces of electric charge on the fluid and the fluid's own surface tension. Desirably, the charge on the fluid overcomes the surface tension and at the tip of the Taylor cone, a thin jet of fluid forms and subsequently and rapidly separates a short distance beyond the tip into an aerosol. Studies have shown that this aerosol (often described as a soft cloud) has a fairly uniform droplet size and a high velocity leaving the tip but that it quickly decelerates to a very low velocity a short distance beyond the tip.

EHD sprayers produce charged droplets at the tip of the nozzle. Depending on the use, these charged droplets can be partially or fully neutralized (with a reference or discharge electrode in the sprayer device) or not. The typical applications for an EHD sprayer without means for discharging or means for partially discharging an aerosol would include a paint sprayer or insecticide sprayer. These types of sprayers may be preferred since the aerosol would have a residual electric charge as it leaves the sprayer so that the droplets would be attracted to and tightly adhere to the surface being coated. However, with EHD apparatus used to deliver therapeutic aerosols, it is preferred that the aerosol be completely electrically neutralized prior to inhalation by the user to permit the aerosol to reach the pulmonary areas where the particular therapeutic formulation is most effective.

The preferred orientation of EHD sprayers is with the nozzle vertical and located above the object to receive the aerosol. This nozzle orientation eliminates, for practical purposes, the problems associated with the fluid dispensed from the nozzle tip collecting on or wicking up the outside of the capillary tube and associated fluid delivery means. If the fluid flows up the outside of the nozzle from the tip, it is no longer available to be sprayed and represents a loss in efficiency of the device. Moreover, fluid on the outside surfaces of the capillary tube may accumulate and suddenly flow back to the tip where it may disrupt the Taylor cone. These disruptions and any other disruptions of the Taylor cone may result in a large variation in the size and size distribution of the aerosol droplets which is particularly undesirable in pulmonary drug delivery.

When administering pharmaceuticals to a patient these limitations on orientation of the EHD apparatus result in either the patients having to tilt their head backwards or to lie on their back when the aerosol is delivered on axis with the nozzle. Alternatively, the EHD apparatus can deliver the aerosol vertically on axis with the nozzle and an elbow means can change the direction of aerosol flow to deliver the aerosol nearly horizontally. With this change in direction of the aerosol, there often is an appreciable loss in the quantity of the aerosol. The loss in quantity is a result of the fluid impacting and depositing on the walls of the delivery device, particularly in the vicinity of the elbow, instead of reaching the patient. One device for reducing disruptions of the Taylor cone and for reducing the loss in quantity of fluid impacting the walls is described in a co-owned U.S. patent application filed of even date herewith and entitled "High Mass Transfer EHD Aerosol Sprayer", which application is hereby incorporated by reference. Therefore, an EHD aerosol sprayer is needed where the aerosol delivery direction can be controlled and wherein the Taylor cone can be stabilized to prevent disruption. Of particular need, is an EHD aerosol sprayer that can spray substantially horizontally and deliver the aerosol without appreciable wetting of the delivery device.

SUMMARY OF THE INVENTION

The invention described herein provides an aerosol delivery method and system for solving the problems discussed above by producing a charged EHD aerosol, discharging the aerosol and inducing a flow in the discharged aerosol in a desired direction without substantial wetting of the device.

In a preferred embodiment the delivery system includes a spray nozzle for dispensing the fluid to be aerosolized and negatively charging the aerosol droplets, a discharge electrode generally proximate the spray nozzle for generating a positive ion stream which intercepts and electrically neutralizes the negative aerosol droplets while also imparting a desired movement on the aerosol in a direction generally away from the discharge electrode, and at least one first reference electrode between the spray nozzle and the discharge electrode for modifying the electric field between the spray nozzle and the discharge electrode. Preferably, the discharge electrode is positioned proximate the spray nozzle such that the ion cloud intercepts the aerosol at a short distance, for example less than about 4 centimeters and more preferably less than 2 centimeters from the spray nozzle tip before the aerosol cloud has had a chance to disperse to a large degree.

Optionally, at least one second reference electrode may be placed near the discharge electrode on the side opposite of the first electrode. Optionally, at least one third electrode may also be placed near the spray nozzle on the side opposite the first reference electrode.

The spray nozzle is usually placed at a potential of between one and twenty kilovolts, with three to six kilovolts being the preferred voltage range. The placing of a negative potential on the spray nozzle results in the aerosol being negatively charged. To electrically discharge the aerosol, a positive potential of between one and twenty kilovolts, and with a preferred voltage of three to six kilovolts, is placed on a discharge electrode. The charges could be reversed on the spray nozzle and the discharge electrode, however, the positive ions from the discharge electrode appear to be much more effective than would negative ions in imparting movement (induced flow) to the aerosol.

Preferably, the discharge electrode includes a sharp point or edge where a positively charged ion cloud is originated to discharge the aerosol and move it in the desired direction. In a preferred embodiment, the axis of the spray nozzle and the axis of the discharge electrode are at an angle of less than about 120 degrees (between 0 degrees and 180 degrees) and more preferably in the range of 30–90 degrees. Larger angles may also be useful, but at angles approaching 180 degrees (the electrodes thereby being substantially opposed) the movement of the aerosol would be substantially toward the spray nozzle. In most uses, this would not be desirable to direct the charged aerosol substantially toward the discharge electrode, as the droplets are readily attracted to the electrode surface which reduces the aerosol delivery efficiency of the sprayer. If the discharge electrode becomes wetted with aerosol under these conditions, an undesired secondary spray can result at the discharge electrode. It is also undesirable to direct the discharge ion cloud substantially toward the spray nozzle as these ions can disrupt the EHD aerosol generation process.

Between the spray nozzle and the discharge electrode is a first reference electrode. The first reference electrode may be a wire, screen, plate or tube, but preferably has a shape that may influence an air stream to move past the spray nozzle. The first electrode may be on but one side of the spray nozzle near the discharge electrode or it may substantially surround the spray nozzle. Preferably, the first reference electrode intersects or breaks the line of sight between the tip of the nozzle and the tip of the discharge electrode to some what de-couple the nozzle's electric field from the electric field of the discharge electrode. By somewhat de-coupling these two electric fields, the attraction of the negatively charged aerosol to the positively charged discharge electrode is minimized. Consequently, the discharge electrode remains predominantly dry. Thus, the accumulation of the aerosol on the discharge electrode does not present a problem from the standpoint of reducing the quality and quantity of the aerosol delivered to the user.

The EHD device is constructed such that gas (generally air) is allowed to enter the device and to then flow near the spray nozzle toward the tip and past the Taylor cone. This gas flow has been found to stabilize the Taylor cone and to move the aerosol away from the tip of the spray nozzle. Moving the charged aerosol away from the tip seems to aid the aerosolization phenomenon at the Taylor cone. Preferably, the corona wind from the discharge electrode is used to assist in inducing the gas flow over the Taylor cone. The positively charged ion cloud downstream from the spray tip readily attracts the negatively charged aerosol droplets away from the nozzle. The motion of the aerosol droplets also induces gas flow over the spray tip and over the Taylor cone.

A preferred embodiment of the delivery method includes dispensing a fluid through a negatively charged spray nozzle to produce negatively charged aerosol droplets by the EHD process, generating a positive ion stream from a positively charged discharge electrode generally proximate the spray nozzle such that the ion stream intercepts and electrically neutralizes the negative aerosol droplets downstream of the spray nozzle while also imparting a desired movement on the aerosol in a direction generally away from the discharge electrode, and inserting a reference electrode between the spray nozzle and the discharge electrode for modifying the electric field between the spray nozzle and the discharge electrode. Preferably, the method further includes orienting the axis of the spray nozzle and the axis of the discharge electrode at an angle of less than about 120 degrees and more preferable in the range of 30–90 degrees. Preferably, the ion cloud intercepts the aerosol at a short distance, for example less than about 4 centimeters and more preferably less than 2 centimeters, from the spray nozzle tip before the aerosol cloud has had a chance to disperse to a large degree.

Another preferred embodiment of the delivery method includes dispensing a fluid through a negatively charged spray nozzle to produce negatively charged aerosol droplets from a Taylor cone in an EHD process, generating a positive ion stream around a positively charged discharge electrode generally proximate the spray nozzle such that the ion stream intercepts and electrically neutralizes the negative aerosol droplets downstream of the spray nozzle while also imparting a desired movement on the aerosol in a direction generally away from the discharge electrode, inserting a first reference electrode between the spray nozzle and the discharge electrode for modifying the electric field between the spray nozzle and the discharge electrode, providing a gas flow path near the Taylor cone between the spray nozzle and the first reference electrode and inducing gas flow past the spray nozzle along the gas flow path.

The EHD apparatus and method is a preferred application of the invention wherein the aerosol is charged. As described earlier, however, the invention is also useful for delivery of many other aerosol products (e.g. fragrances, lubricants, etc). In these other uses it may be useful to move an uncharged aerosol. In this case, the discharge electrode described herein may more accurately be termed an "ionization electrode" because the ions do not discharge the charge on the aerosol, but merely provide the momentum or the corona wind to direct the flow in the desired direction. Apparatus according to the invention would include aerosol source, an ionization electrode for developing the corona wind along a desired path, a reference electrode and a voltage source.

In any of the applications of the invention the corona wind could either be a positive or negative ion stream, though the positive stream seems to have some advantages in the drug delivery applications.

BRIEF DESCRIPTION OF THE DRAWINGS

The accompanying drawing incorporated in and forming part of the specification illustrates several aspects of the present invention, and together with the description serve to explain the principles of the invention. In the drawings.

Figure 1:
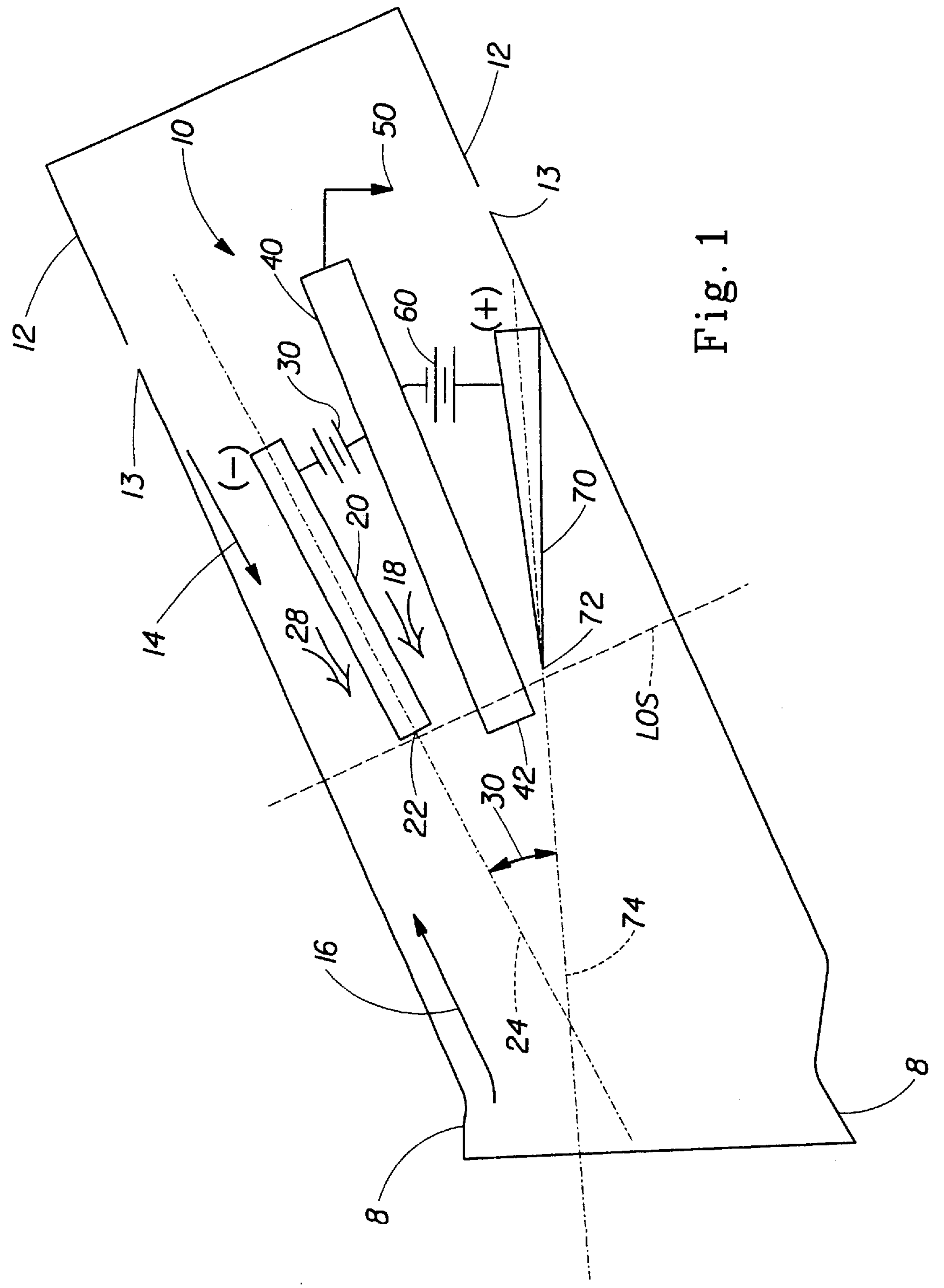
FIG. 1 is a schematic of an EHD sprayer in accordance with the present preferred embodiment of the invention.

Reference will now be made in detail to the present preferred embodiment of the invention, examples of which are illustrated in the accompanying drawings.

DETAILED DESCRIPTION OF THE PREFERRED EMBODIMENT

The invention includes methods and apparatus for directionally controlling the delivery of an aerosol along a desired path. The aerosol may be created by any number of known means (for example, by vaporization, nebulization, electrospraying, expansion through an orifice, and the like) and may have an electrical charge or not. One preferred method of creating the aerosol is by electospraying and particularly by electrohydrodynamic spraying. The purpose of the induced flow electrohydrodynamic (EHD) aerosol sprayer is to provide a device that will permit an operator to consistently spray an aerosol horizontally or in any other arbitrary direction, in the absence of other external airflow. The sprayer utilizes electrical means for stabilizing the Taylor cone with a gas flow near the Taylor cone and for directionally controlling the movement of the charged aerosol generally in a direction controlled by the position and orientation of the discharge electrode and the reference electrode.

The aerosol delivery system and method are particularly useful for delivering therapeutic agents by inhalation. They are even more useful for delivering therapeutic agents into the lungs. Therapeutic agents include any materials that are beneficial to the user. Particularly useful therapeutic agents include not only pharmaceuticals but also, for example, chemotherapeutic or chemopreventive agents, vaccines, nucleic acids, proteins and gene therapy agents.

Though the invention is described in sufficient detail to enable others to practice it, and though not bound to a description of the manner in which the invention works, nevertheless the inventors believe that the movement of the aerosol away from the discharge electrode is due to the effect of what is termed a corona wind or induced air flow. It is believed that the corona wind works in the following way. The positive charge on the discharge electrode results in corona or ionization of the nearby air molecules producing a positive ion cloud around the electrode. The like-charged ions repel and cause a migration of these ionized air molecules away from the discharge electrode. As is well understood in the art, a sharp point or edge on the discharge electrode (which would be one of our preferred embodiments of the discharge electrode) substantially increases the corona and the movement of the ions away from the point or edge. Since these air molecules have mass, their movement causes a corona wind effect or induced air flow directly away from the discharge electrode (rather axially to a sharp point or edge of the discharge electrode), which then intercepts the aerosol droplets downstream of the tip of the nozzle and redirects them (imparts momentum) generally along the path of the corona wind. As earlier noted, the positively charged air molecules also serve to neutralize/discharge the negative charge on the aerosol. Since the corona wind from the discharge electrode moves along the axis of and away from the discharge electrode, the orientation of the discharge electrode substantially determines the direction taken by the aerosol.

By providing an air flow path alongside of the spray nozzle, it has also been found that as the corona wind moves the aerosol away from the spray nozzle, an induced airflow is caused along the spray nozzle and past the Taylor cone. This induced airflow seems to stabilize the Taylor cone, particularly as the EHD device is operated in different orientations. The induced airflow seems to improve the aerosolization process by preventing wicking of the fluid on the outside of the spray nozzle and by transporting the charged aerosol droplets away from the region downstream of the spray nozzle. It may also provide an air curtain that centers the Taylor cone, though this is not proven yet. The induced airflow is beneficial whether the corona wind is created on but one side of the spray nozzle or at several sites or substantially all around the spray nozzle with single or multiple discharge electrodes and reference electrodes.

FIG. 1 provides a schematic of the preferred embodiment of the induced flow EHD aerosol sprayer 10. In this embodiment, the basic sprayer 10 has housing wall 12 terminating in an exit mouthpiece 8, a spray nozzle 20 having a central axis 24, a first reference electrode 40, and discharge electrode 70 having a central axis 74. The exit mouthpiece 8 generally has a contour allowing the user to bring the aerosol sprayer into contact with the lips or mouth area and receive the aerosol through the mouth for treatment of the lungs. The DC voltage source 30 electrically connects and maintains the spray nozzle 20 at a negative voltage with respect to reference electrode 40. A second DC voltage source 60 electrically connects and maintains the discharge electrode 70 at a positive voltage with respect to reference electrode 40. Ground 50 maintains reference electrode 40 at a ground reference voltage, approximately zero volts DC. It will be understood that the reference electrode 40 is conveniently at ground potential, but that it could be at any potential that is negative with respect to the discharge electrode and positive with respect to the spray nozzle. Moreover, the polarity of the charge on the spray nozzle and discharge electrode are conveniently negative and positive respectively, but it is only necessary that the charges are negative and positive with respect to each other (and the reference electrode).

Spray nozzle 20 is typically a capillary tube or other tube, plate or any other shape used to deliver fluid in EHD applications. In some embodiments the tube used for spray nozzle 20 may have a spray tip 22 which may be designed specifically for EHD spray applications. These tips promote the formation and stability of the Taylor cone. A stable Taylor cone tends to reduce the deviation in the droplet size in the resulting aerosol. The invention includes apparatus including a single spray nozzle that can produce multiple Taylor cones and apparatus with multiple spray nozzles.

Figure 7B:
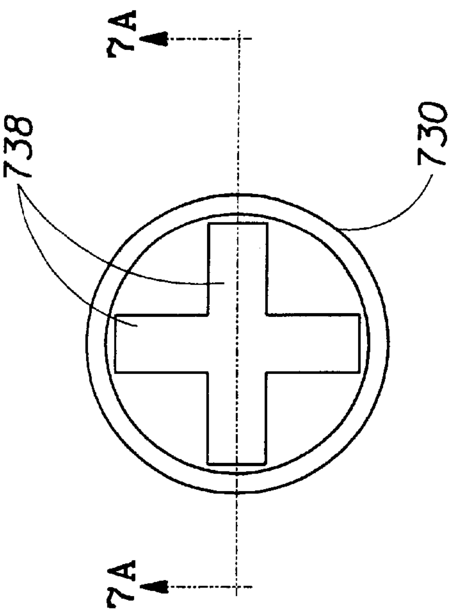
FIGS. 7A and 7B show cross sectional views of preferred spray tips used in delivering fluid to an EHD sprayer.
Figure 7A:
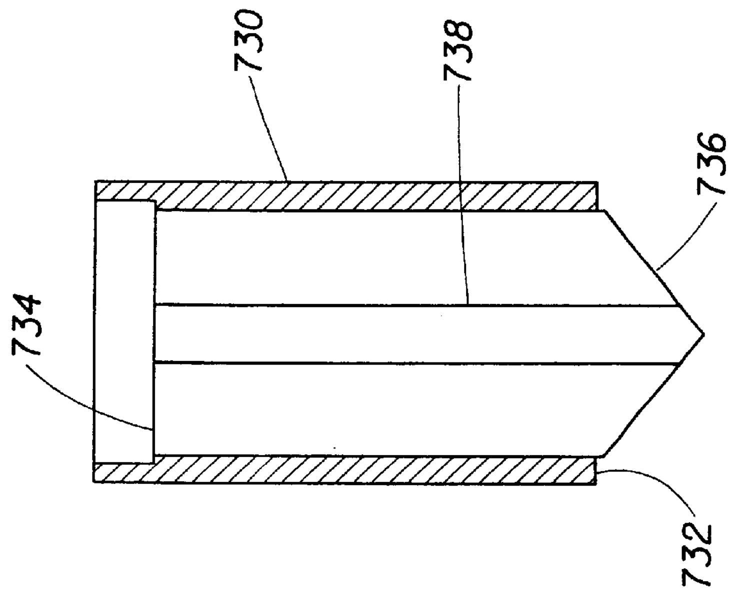

One preferred spray nozzle design is shown in FIGS. 7A and 7B. Each spray nozzle 730 includes a round tube having a spray tip 732 at one end and a connection to the source of fluid to be aerosolized at the other end. The spray tip can be merely the open end of the spray nozzle or can optionally include other designs or elements to better promote the formation of Taylor cones. In FIGS. 7A and 7B a partitioning plug 734 is secured in the spray nozzle at the spray tip. The partitioning plug 734 is a cylindrical element terminating in a cone 736 that becomes part of the spray tip for creation of the Taylor cone. The partitioning plug is machined to have four ribs 738 and having therefore a cross section in the shape of a cross to provide four paths for the fluid in the spray nozzle. This has been found to improve the formation of the Taylor cone and to increase the throughput of fluid. Other designs may result in one or more Taylor cones at each spray tip. Multiple nozzles in any useful arrangement may be used in the device.

Discharge electrode 70 typically has a sharp discharge tip 72 or a knife-edge or other sharp points or other protrusions. As is known in the art, these sharp shapes tend to promote the formation of ions. Alternatively, any tip shape that is capable of ionizing air molecules may be utilized. The discharge electrode is generally elongated and has a fairly easily definable central axis 74. Whether elongated or not, however, the tip 72 will have a geometry which allows significant ionization in the neighborhood of one or more sites on the discharge electrode and movement of the ions away from these sites in a direction which is predictable and reproducible. When the central axis is easily definable, the direction of movement of the ions and ultimately the aerosol is generally parallel with this axis. When the axis is not easily definable, the direction of movement of the ions and the aerosol is predictable and reproducible away from the sites in a direction that we will define as axial to the discharge sites. Discharge electrodes with multiple ionization sites and multiple discharge electrodes (with or without multiple spray nozzles) are within the scope of the invention.

The discharge electrode is located sufficiently close to the spray nozzle 20 and to the spray tip 22 and is oriented with respect thereto such that the ions from the discharge electrode may intercept the aerosol downstream of the spray tip 22. If the interception point is remote from the spray tip at a point where the aerosol has had sufficient time to become quite disperse, the effect of the ion cloud to move the aerosol in the desired direction is diminished. Therefore, the discharge electrode is preferably located sufficiently close to the spray nozzle 20 and to the spray tip 22 and is oriented with respect thereto such that the ions from the discharge electrode may intercept the aerosol proximate the spray tip 22 before the aerosol has dispersed to any great degree.

A reference electrode 40 is located between spray nozzle 20 and discharge electrode 70. This reference electrode can be a wire, screen, plate, tube or other shape with modifies the field between the spray nozzle and the discharge electrode. When used for influencing the flow of air near the spray nozzle and the Taylor cone, the reference electrode preferably has a shape and size sufficient for that purpose. In some embodiments, the spray end 42 of reference electrode 40 may be located proximate but not intersecting the line LOS that connects the spray tip 22 to discharge tip 72. In other embodiments, the spray end 42 of reference electrode 40 may be located to barely intersect the line LOS. In a preferred embodiment, however, the reference electrode 40 is positioned so that it crosses line LOS and the spray end 42 is past the line LOS but not substantially within the region of the aerosol spray downstream of the spray nozzle during use. With the reference electrode in this preferred position, the electric field generated between the spray nozzle 20 and reference electrode 40 is substantially de-coupled from the electric field generated between the discharge electrode 70 and reference electrode 40. Thus, changes in the relative position of the spray nozzle 20 with respect to reference electrode 40 or changes in the electric field strength generated between the spray nozzle 20 and reference electrode 40 have little, if any, impact on the electric field generated between the discharge electrode 70 and the reference electrode 40. Similarly, changes in the relative position of the discharge electrode 70 with respect to reference electrode 40 or changes in the electric field strength generated between the discharge electrode 70 and reference electrode 40 have little, if any, impact on the electric field generated between the spray nozzle 20 and the reference electrode 40.

However, the existence and the position of the reference electrode contribute with the discharge electrode to controlling the direction of the aerosol delivery. Without the reference electrode, the charged aerosol would tend to be attracted toward the tip of the discharge electrode. The positive ions from the tip of the discharge electrode would also be attracted toward the aerosol and the spray nozzle and the spray nozzle tip. The aerosol and the positive ions would then tend to meet substantially in between the spray nozzle and the discharge electrode. The reference electrode is positioned such that it reduces this tendency so that the aerosol and the positive ions intersect more near the intersection of their respective central axes downstream of the electrodes. In FIG. 1, the discharge electrode is positioned such that the aerosol is moved generally in the direction of the positive ion flow and toward the exit mouthpiece 8 and the user.

The discharge electrode 20 and the reference electrode 40 are fixed in the EHD device in such a manner and with respect to the spray nozzle 20 such that a gas flow path (such as at 18 and/or 28) is provided alongside the spray nozzle. For example, in FIG. 1, the electrodes are fastened such that air may enter the EHD device through the mouthpiece 8 in the housing 12 and move along the inside of the housing wall at 16 and then along the gas flow path at 18 and/or 28. When used to deliver therapeutic agents by inhalation, the user's mouth would typically cover the mouthpiece so that additional openings 13 may be necessary in the housing 12 to allow entry of gas or air. The position of the openings 13 may be moved to allow more or less gas to move along the gas flow paths 18 and 28. This air movement along the gas flow path 18 and/or 28 has been found to contribute to a very stable Taylor cone at the tip 22. The airflow also helps move the aerosol to the location where the positive ions from the discharge electrode impact the aerosol. The airflow along the path 18 and/or 28 appears to be at least partially induced by the corona wind from discharge electrode 70.

Preferably, reference electrode 40 and spray nozzle 20 are positioned such that the electric field intensity is largest between spray tip 22 and spray end 42, as for example when they are angled toward each other and the spray tip 22 and the spray end 42 are relatively closer together than other parts of the electrodes. This relative position of spray nozzle 20 and reference electrode 40 minimizes any tendency for the dispensed fluid to coat or collect on the outside of spray nozzle 20. It also has some positive effect on the induced air flow past at 18 and/or 28 due to the corona wind. Collection of fluid on the outside of spray nozzle 20 (with the spray nozzle fairly vertical and the nozzle tip at substantially the lowest point) is most likely when the spray nozzle 20 dispenses the aerosol in the upward direction and is least likely when the spray nozzle 20 dispenses the aerosol in the downward direction. Collection of fluid reduces the quantity of the fluid that is converted into an aerosol. Additionally, this fluid collection has the potential to disrupt or interfere with the Taylor cone. Any disruption or interference with this cone affects the aerosol droplet size and the droplet size distribution. This relative position of spray nozzle 20 and reference electrode 40 also minimizes the tendency for the aerosol to coat or collect on the reference electrode 40. Any collection of the aerosol on the reference electrode 40 reduces the quantity of aerosol delivered to the user from the EHD aerosol sprayer 10.

For the above mentioned reasons it is desirable to orient the spray nozzle more in a vertical orientation (generally above the horizontal) so that the fluid is restrained by gravity from wicking up the nozzle and the aerosol generally moves downward away from the tip. This also suggests that the movement of the corona wind is most beneficially away from the nozzle tip 22 such as when the central axis 74 of the discharge electrode is oriented parallel to the central axis 24 of the nozzle or at some acute angle. Of course, the corona wind must intercept the aerosol in some manner to affect the direction of the aerosol.

When used to deliver therapeutic agents by inhalation, it is also desirable to deliver an aerosol horizontally to the user's mouth. This desire suggests that it would be more beneficial to shift the direction of the aerosol by up to 90 degrees so that it is delivered substantially horizontally to the user. Both of these desires may be accomplished by maintaining an angle 30 between the nozzle central axis 24 and the discharge electrode central axis 74 between about 0 and 120 degrees. The invention will continue to work at angles in excess of 120 degrees, but it will be understood that the aerosol will be redirected by the corona wind more in the general direction of the nozzle at these higher angles. Ultimately, at 180 degrees, the corona wind would be moving substantially parallel to the nozzle central axis and may substantially defeat the purpose of the invention as described earlier. The aerosol is most preferably directed by the discharge electrode toward the mouthpiece 8 and ultimately to the user contacting the mouthpiece. It may be useful when the angle 30 is a large number to use more than one reference electrode 40 between the spray nozzle and the discharge electrode.

Also, the best results in inducing airflow past the Taylor cone have been observed when the discharge electrode is oriented so that the corona wind moves in a direction substantially away from the spray nozzle. This may be accomplished by maintaining an angle 30 between the nozzle central axis 24 and the discharge electrode central axis 74 between about 0 and 90 degrees, preferably between 0 and 60 degrees.

The discharge electrode tip 72 may be located either upstream or downstream of the spray tip 22. As mentioned earlier, in this upstream or downstream position proximate spray tip 22, the ions from the discharge electrode may intercept the aerosol a short distance downstream of the spray tip 22 before the aerosol has dispersed to any great degree. Preferably, the discharge electrode is positioned proximate the spray nozzle such that the ion cloud intercepts the aerosol at a distance of less than about 4 centimeters and more preferably less than 2 centimeters from the spray nozzle tip before the aerosol cloud has had a chance to disperse to a large degree. By the term "upstream" of the spray tip 22, we mean that when the spray nozzle is in a vertical orientation, the discharge electrode tip is above a plane through the spray tip 22 perpendicular to the nozzle central axis 24. By the term "downstream" we mean that the discharge electrode tip would be below the perpendicular line under the above conditions. Whether the discharge electrode is positioned upstream or downstream of the spray nozzle, the discharge electrode should be located outside of the spray path of the aerosol. As mentioned, this spray path tends to enlarge greatly as the aerosol disperses downstream of the spray nozzle.

Preferably, reference electrode 40 and discharge electrode 70 are positioned such that the electric field intensity is largest between spray end 42 and discharge tip 72. This relative position of discharge electrode 70 and reference electrode 40 minimizes the quantity of ionized air molecules that flow to the ground electrode 40. Thus, this configuration maximizes the number of ionized air molecules (corona wind) available to discharge the aerosol. Additionally, this configuration also tends to maximize the aerosol quantity that moves with the corona wind and the induced air flow past the Taylor cone.

DC voltage source 30 electrically connects spray nozzle 20 to reference electrode 40 and maintains spray nozzle 20 at a negative potential. DC voltage source 60 electrically connects discharge electrode 70 to reference electrode 40 and maintains discharge electrode 70 at a positive potential. A positive potential is preferred on the discharge electrode 70 to form the corona wind discussed above. A negative voltage on the discharge electrode 70 would more readily form an ion stream. However, these negative ions (electrons) have a higher mobility (velocity) than air molecules, but they also have a very small mass. Thus, electrons have far less momentum than air molecules so that using electrons to discharge the aerosol would have relatively little impact on the movement of the aerosol but in some applications may be useful.

The positive voltage on the discharge electrode 70 strips an electron from an air molecule leaving the air molecule with a positive charge. Consequently, the ionized air molecule will move by repulsion away from the discharge electrode 70. Additionally, the ionized air molecules are attracted to the negative charge on the aerosol. In the embodiments where the reference electrode 40 does not cross line LOS, the ionized air molecule will also be attracted to the negative voltage on the spray nozzle 20. Due to the aerosol's closer proximity most, if not all, of the ionized air interacts with the aerosol. Thus, the predominate motion direction of the ionized air molecules is determined by the orientation of the ionization sites on the discharge electrode, which is typically directly away from the discharge electrode 70 and generally parallel to the central axis 74. Consequently, the aerosol also moves in the same direction as determined by the characteristics and/or position/orientation of the discharge electrode 70.

Voltage sources 30 and 60 typically provide between one and twenty kilovolts, with the preferred voltage being between three and six kilovolts. The best voltage for aerosolizing a particular fluid depends on the fluid's properties, principally the conductivity/resistivity, viscosity, surface tension, and flow rate. Additionally, the relative positions of the spray nozzle 20, reference electrode 40, and discharge electrode 70 will typically have some influence on the best voltage(s) to be applied to the spray nozzle 20 and discharge electrode 70. Furthermore, the type of nozzle tip 22 and the aerosol droplet size will also influence the ideal voltage utilized in a particular application. To some extent, the magnitude of the voltage may be used to control the velocity of the ions from the discharge electrode. The person of ordinary skill in the art of designing and using EHD sprayers is familiar with typical voltages utilized for specific fluids and equipment geometry.

In some embodiments, the addition of a resistance in series with the voltage sources 30 and/or 60 may be required to prevent arcing between the spray nozzle 20 and reference electrode 40, or between reference electrode 40 and discharge electrode 70. The resistance is intended to limit current so that arcing is either minimized or cannot be maintained. To be effective without overly limiting the current to the electrodes, the resistance should have a value of hundreds of kilohms to hundreds of megohms. In a preferred embodiment and operating at preferred voltages, the resistance has a value between about ten and twenty megohms.

Ground 50 maintains the reference electrode 40 at a reference voltage. Preferably, this reference voltage is approximately zero volts. Preferably, the reference electrode is electrically paired with the nozzle and the discharge electrode. However, in some applications, the "reference electrode" is not an electrode at all and may instead be made of a dielectric material. This may promote wetting of the dielectric "reference electrode" by charged aerosol; however, if the application is one that only requires a short burst of aerosol (perhaps several seconds), then this dielectric "reference electrode" may still function.

Figure 2:
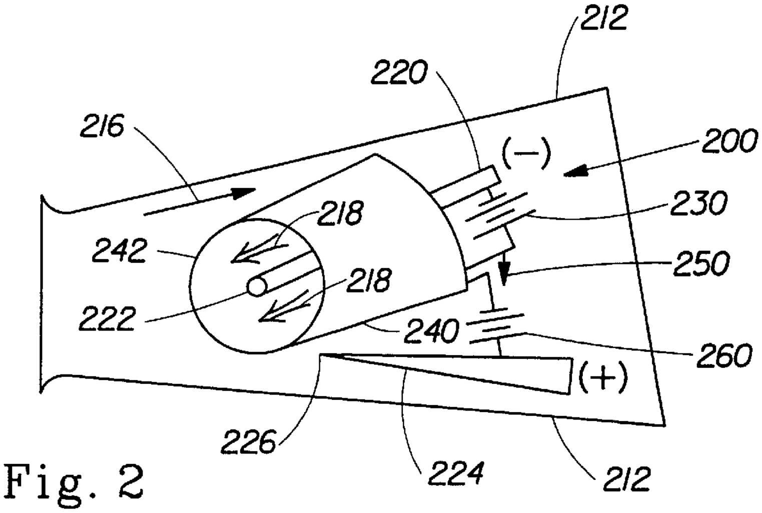
FIG. 2 is a schematic of an EHD sprayer in accordance with a second embodiment of the invention.

FIG. 2 illustrates a second EHD sprayer 200 configured to control the aerosol discharge direction. Sprayer 200 employs a spray nozzle 220 that is electrically connected to a reference electrode 240 with a voltage source 230. Discharge electrode 224 is connected to reference electrode 240 with a voltage source 260. The spray nozzle 220 and the discharge electrode 224 are similar to spray nozzle 20 and the discharge electrode 70 discussed above. Voltage sources 230 and 260 are also similar to voltage sources 30 or 60 described above. Ground 250 provides the same function and reference voltage to that disclosed above for ground 50. The reference electrode 240 has been modified so that the electric field produced between spray nozzle 220 and reference electrode 240 is symmetric around the outside surface of spray nozzle 220. An airflow path at 218 is created by the reference electrode 240 (which is open to intake airflow at the upstream end nearest the voltage supply and opposite the spray tip 222) and the spray nozzle 220. Air may move up the housing walls 212 at 216 and thence down the flow path 218 past the Taylor cone. When used to deliver therapeutic agents by inhalation, the user's mouth would typically cover the mouthpiece so that additional openings (similar to the openings 13 in FIG. 1) may be necessary in the housing 212 to allow entry of gas or air.

Preferably, reference electrode 240, the spray nozzle 220 and the discharge tip 226 are positioned such that the electric field intensity is largest between spray tip 222 and spray end 242 and between the spray end 242 and the discharge tip 226. This relative position of spray nozzle 220 and ground electrode 240 minimizes any tendency for the fluid dispensed to coat or collect on the outside of spray nozzle 220. The fluid collection on the outside of spray nozzle 220 is most likely when the spray nozzle 220 dispenses the aerosol in the upward direction, and is least likely when the spray nozzle 220 dispenses the aerosol in the downward direction. The collection of fluid reduces the quantity of the fluid that is converted into an aerosol. Additionally, this fluid collection has the potential to disrupt or interfere with the Taylor cone. Any disruption or interference with this cone affects the aerosol droplet size and the droplet size distribution.

The positioning of the spray tip 222 with respect to spray end 242 of the reference electrode 240 is fairly important in minimizing the tendency for the aerosol to coat or collect on the ground electrode 240. A preferred position of the reference electrode would be such that the spray end is approximately on the line of sight between the spray nozzle tip 222 and the discharge tip 226. Positioning the reference electrode a short distance from this line of sight is still useful and part of the invention; however, as the position of the reference electrode is changed (back toward the voltage source in FIG. 2) to expose more of the spray nozzle, the aerosol tends to move toward the discharge electrode and to neutralize and coat the discharge electrode more. If the position of the reference electrode is changed to more cross over the line of sight (that is, to more surround the spray nozzle tip and shield it from the discharge electrode) the tendency is for the aerosol to coat the inside of the reference electrode.

The preferred shape for spray nozzle 220 is a cylindrical tube. Consequently, the preferred shape for the reference electrode 240 is a truncated cone with the smaller diameter opening forming spray end 242. This configuration of sprayer 200 provides an approximately conical electrical field between spray tip 222 and spray end 242. Other sprayer 200 geometry could also generate symmetric diverging electric fields. These electric fields cause the aerosol to move away from sprayer 200, with the motion direction aligned generally with the longitudinal axis of spray nozzle 220.

Figure 3:
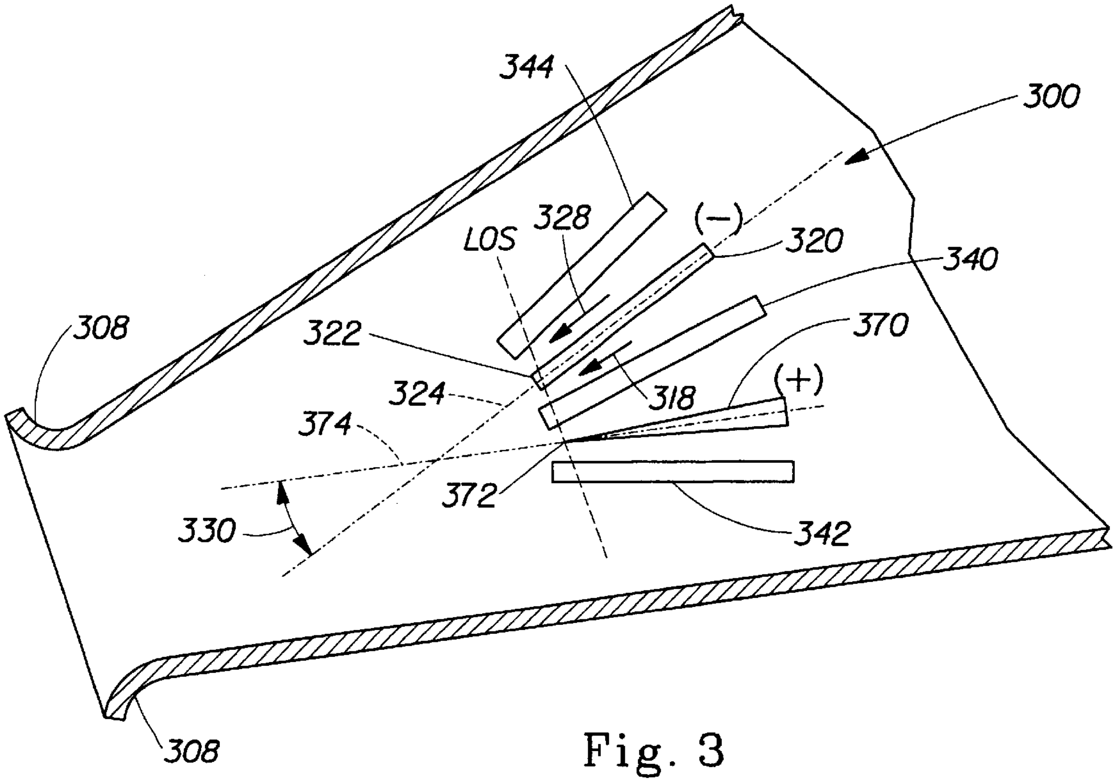
FIG. 3 is a schematic of an EHD sprayer in accordance with a third embodiment of the invention

FIG. 3 illustrates a third EHD sprayer 300 configured to control the aerosol discharge direction and stabilize the Taylor cone. Sprayer 300 employs a spray nozzle 320 that is electrically connected to a first reference electrode 340 with a voltage source (not shown) to provide a negative charge on the spray nozzle with respect to the first reference electrode 340. Discharge electrode 370 is connected to a voltage source (not shown) which places a positive charge on the discharge electrode with respect to the first reference electrode 340. The spray nozzle 320 and the discharge electrode 370 are similar to spray nozzle 20 and the discharge electrode 70 discussed above. The voltage sources are also similar to voltage sources 30 or 60 described above. Positive ions are created at the tip 372 of the discharge electrode and a corona wind is created in a direction substantially along the axis 374 toward the mouthpiece 308 of the device.

The embodiment of FIG. 3 also incorporates a second reference electrode 342 near the discharge electrode on the side opposite the first reference electrode 340 and a third reference electrode 344 near the spray nozzle on the side opposite the first reference electrode. Reference electrodes 340, 344 and spray nozzle 320 create an air flow path at 318 and 328 respectively. Air is induced at least partially by the corona discharge to move down the flow path 318 and 328 past the Taylor cone to provide stability. Furthermore, reference electrodes 340, 344 and spray nozzle 320 provide greater symmetry in the electric field or spray tip 342 than what can be achieved in spray nozzle 20. Likewise, reference electrodes 340, 342 and discharge electrode 370 provide symmetry in the electric field at discharge tip 372 so that positive ions are more likely to move along axis 374 than in the sprayer shown in FIG. 1.

The EHD sprayers shown in FIGS. 1–3 may be arranged into an EHD sprayer employing multiple spray nozzles. Utilizing multiple spray nozzles permits an EHD sprayer to aerosolize greater volumes of fluid required in many aerosol sprayer applications. These spray nozzles may be arranged in any shape or array desired as long as the electric field interactions are taken in to account. The nozzles may be arranged in circles, lines, multiple stacked lines or random stacks may be used, for example.

Figure 4:
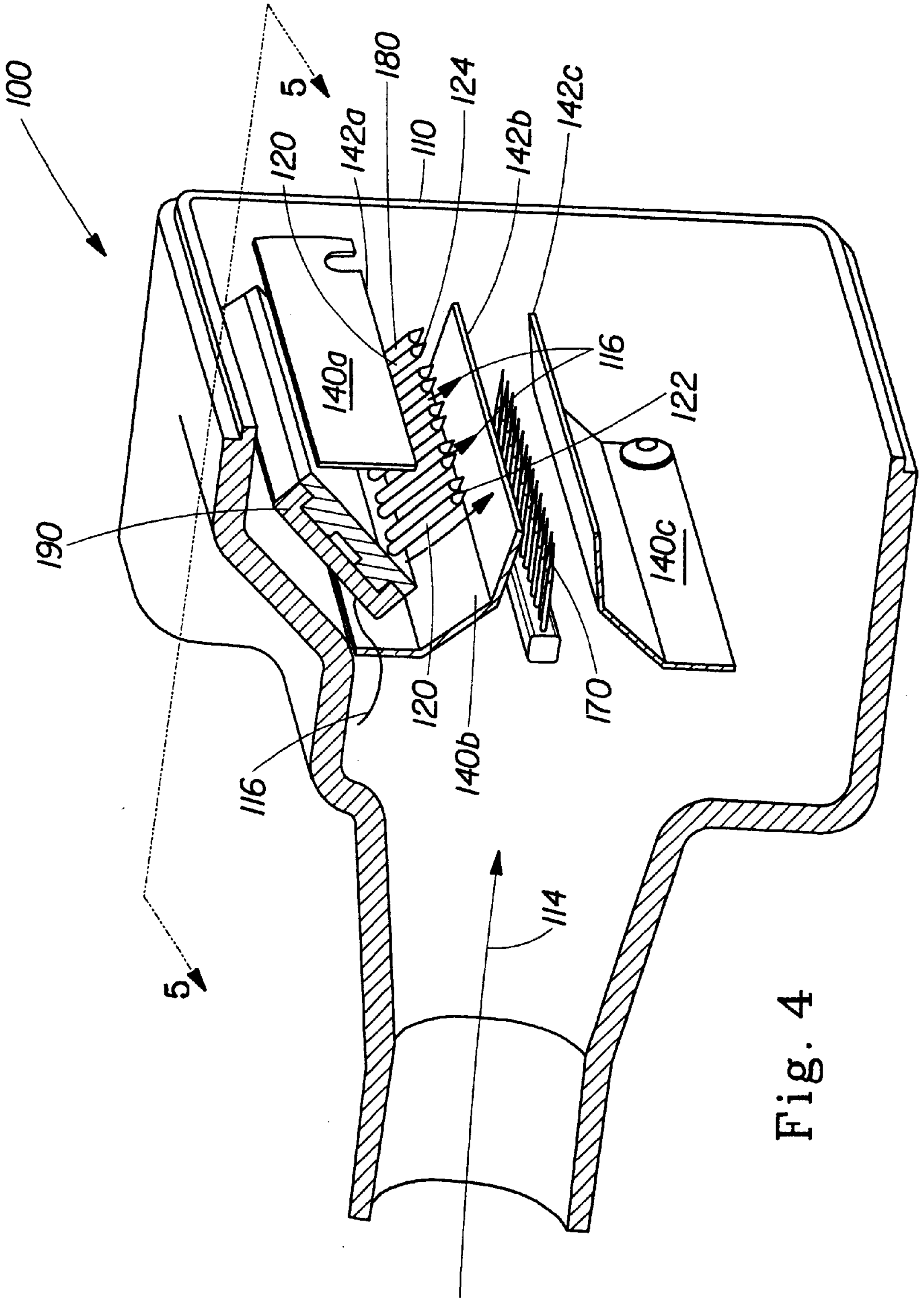
FIG. 4 is an orthographic cutaway view of a multi-nozzle EHD sprayer in accordance with the present invention.
Figure 5:
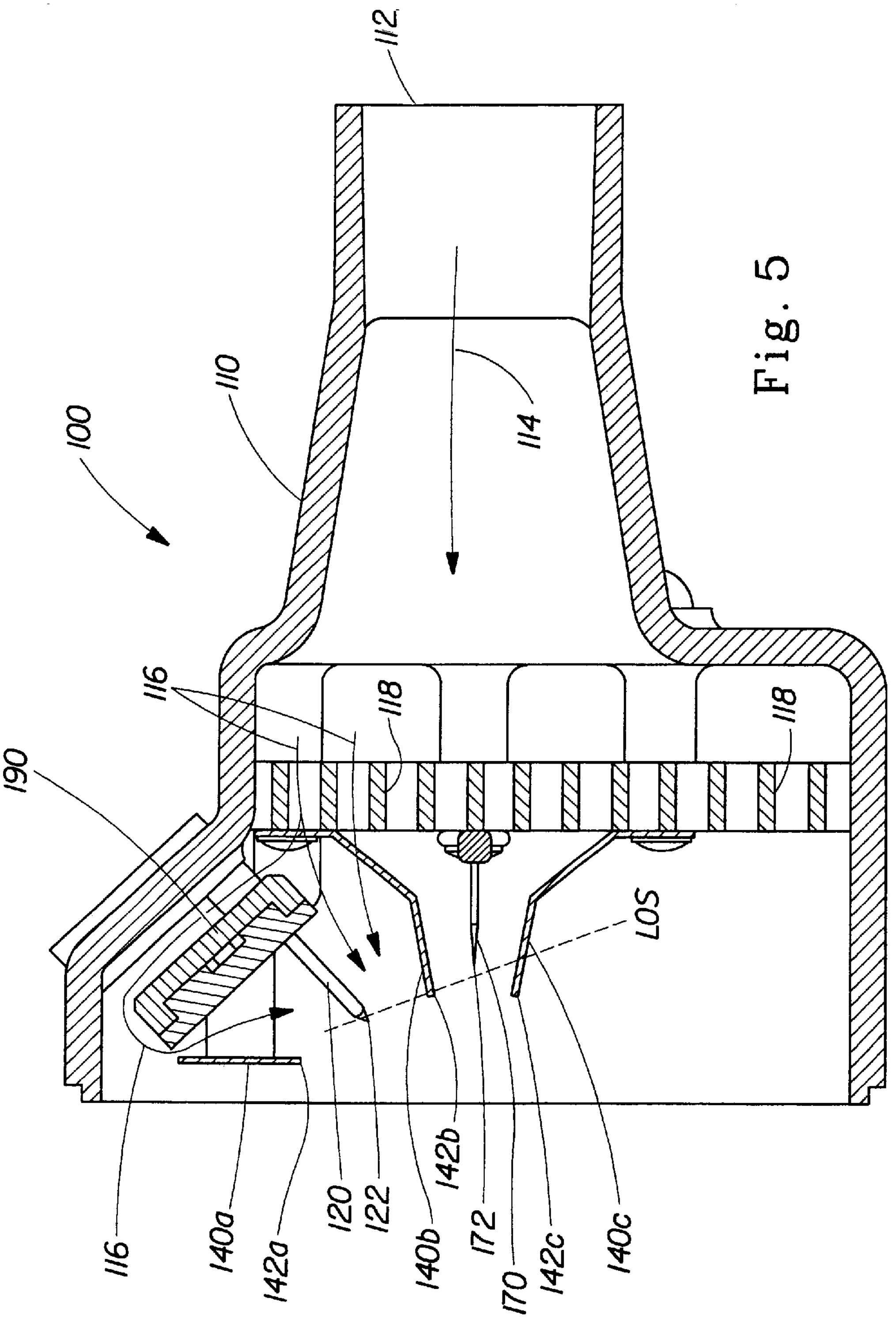
FIG. 5 is a side view of the multi-nozzle sprayer shown in FIG. 4 taken at 5—5.
Figure 6:
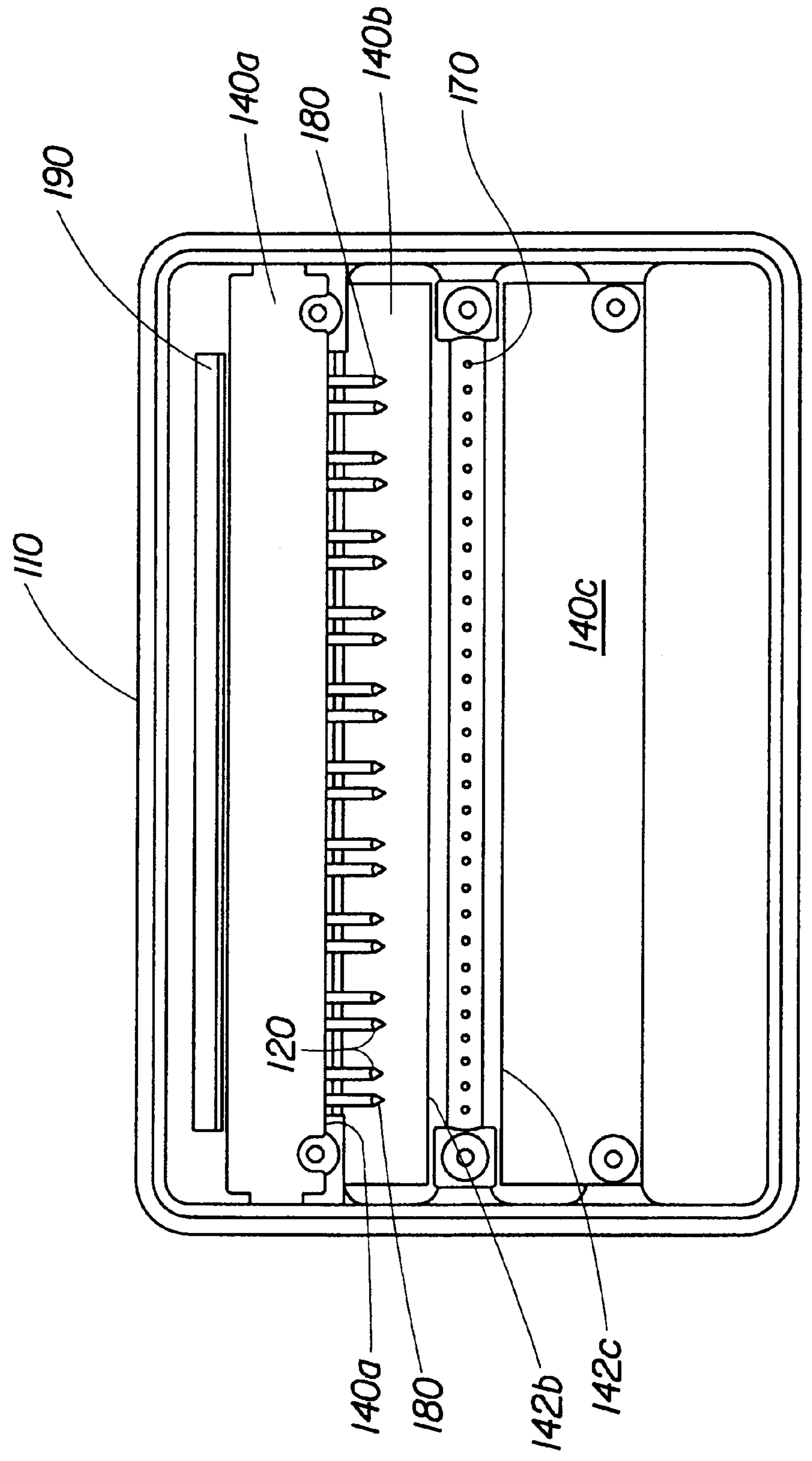
FIG. 6 is a front view of the multi-nozzle sprayer shown in FIG. 4.

An exemplary multiple nozzle configuration is illustrated in FIGS. 4–6. These figures illustrate a linear spray nozzle array in a device for pulmonary delivery of drugs in a clinical setting where the source of fluid to be aerosolized is remote from the EHD sprayer. An EHD sprayer is housed in a device 100 remote from the source of fluid. The EHD sprayer 100 shown in FIGS. 4–6 includes a housing 110, air inlet 112, spray nozzles 120, reference electrodes 140, discharge electrodes 170, spray electrodes 180, and manifold 190. A DC voltage source (see FIG. 1) electrically connects and maintains the spray nozzles 120 at a negative voltage with respect to reference electrodes 140. A second DC voltage source (see FIG. 1) electrically connects and maintains the discharge electrodes 170 at a positive voltage with respect to reference electrodes 140. Ground (see FIG. 1) maintains reference electrodes 140 at a ground reference voltage (approximately zero volts DC). The housing 110 contains and supports the spray nozzles 120, ground electrodes 140, discharge electrodes 170, spray electrodes 180, and manifold 190. All of these elements are supported by the housing 110 so that air can enter the housing such as at 114 and through holes in perforated plate 118 so as to be available above the reference electrodes 140 to be induced by the corona wind along the gas flow path 116 past the spray nozzles 120 and past the Taylor cones produced at the tip 122 of the spray nozzles. Additionally, housing 110 may contain the voltage source(s) or provide connections for external voltage source(s).

Each spray nozzle 120 is typically a capillary tube or other tube, electrode or other shape used to deliver fluid in EHD applications. In some embodiments the tube used for a spray nozzle 120 may have a spray tip 122 designed specifically for EHD spray applications. This tip promotes the Taylor cone formation. Additionally, this tip may stabilize the Taylor cone, which consequently tends to reduce the deviation in the droplet size in the resulting aerosol. The induced airflow along the gas flow path 116 additionally stabilizes the Taylor cone.

Each discharge electrode 170 typically has a knife edge or needle like discharge tip 172. These tip shapes tend to promote the formation of ionized air molecules. Alternatively, any tip shape that is capable of ionizing air molecules may be utilized.

In many uses it is desirable to maintain an angle between the spray nozzle and the discharge electrodes between about 0 and 120 degrees. The invention will continue to work at angles in excess of 120 degrees, but it will be understood that the aerosol will be redirected by the corona wind more in the general direction of the nozzle at these higher angles. Ultimately, at 180 degrees, the corona wind would be moving substantially parallel to the nozzle central axis and would potentially move the aerosol back to the nozzle. This would substantially defeat the purpose of the invention. When using multiple spray nozzles and discharge electrodes, it is useful to maintain substantially the same angle between all the spray nozzles and all the discharge electrodes; however, it is sufficient to maintain that angle between any of them such that the overall effect of the corona wind is to move the aerosol away from the spray nozzles toward the desired target/user and/or to induce the flow of air along the gas flow path 116 past the Taylor cone. The spray nozzles and discharge electrodes need not be paired in any one to one relationship.

Also, the best results in inducing airflow past the Taylor cone have been observed when the discharge electrodes are oriented so that the corona wind moves in a direction substantially away from the spray nozzle. This may be accomplished by maintaining an angle between a plane cutting through the nozzles and a plane cutting through the discharge electrodes between about 0 and 90 degrees, preferably between 0 and 60 degrees. And the discharge electrode tips 172 may be located either upstream or downstream of the spray tips 122. As mentioned earlier, in this position upstream or downstream proximate the spray tips 122, the ions from the discharge electrode may intercept the aerosol a short distance from the spray tips 122 before the aerosol has dispersed to any great degree. By the term "upstream" of the spray tips 122, we mean that when the spray nozzles are in a vertical orientation, the discharge electrode tips are above a line drawn through the spray tips 122 perpendicular to a central axis of the spray nozzles. By the term "downstream" we mean that the discharge electrode tips would be below the perpendicular line under the above conditions.

In the embodiment shown, there are three reference electrodes **140*a*, 140*b*, and 140*c*. Other embodiments may use different configurations of reference electrodes 140 as required to develop and shape the electric fields desired for a particular application. Reference electrode 140*a* is located above spray nozzles 120**.

Preferably, reference electrodes **140*a* and 140*b* and spray nozzles 120 are positioned such that the electric field intensity is largest between spray tips 122 and spray ends 142*a* and 142*b*. This relative position of spray nozzles 120 and reference electrodes 140*a* and 140*b* minimizes any tendency for the fluid to coat or collect on the outside of spray nozzles 120. The collection of fluid on the outside of spray nozzles 120 is most likely when the spray nozzles 120 dispense aerosol in the upward direction, and is least likely when the spray nozzles 120 dispense aerosol in the downward direction. The collection of fluid reduces the quantity of the fluid that is converted into an aerosol. Additionally, this fluid collection has the potential to disrupt or interfere with the Taylor cone. Any disruption or interference with this cone affects the aerosol droplet size and the droplet size distribution. This relative position of spray nozzles 120 and reference electrodes 140*a* and 140*b* also minimizes the tendency for the aerosol discharged to coat or collect on the reference electrodes 140*a* and 140*b*. Any collection of the aerosol on the reference electrodes 140*a* and 140*b* reduces the quantity of aerosol discharged from the EHD aerosol sprayer 100**.

Reference electrode **140*b* is also located between spray nozzles 120 and discharge electrodes 170. In some embodiments, the spray end 142*b* of reference electrode 140*b* may be located to intersect the line LOS (see FIG. 1) that connects a spray tip 122 to a discharge tip 172. In the preferred embodiment, however, the reference electrode 140*b* is positioned so that reference electrode 140*b* crosses line LOS (see FIG. 1). With the reference electrode in the preferred position, the electric field generated between the spray nozzles 120 and reference electrode 140*b* is substantially de-coupled from the electric field generated between the discharge electrodes 170 and reference electrode 140*b*. Thus, changes in the relative position of the spray nozzles 120 with respect to reference electrode 140*b*, or changes in the electric field strength generated between the spray nozzles 120 and reference electrode 140*b* have minimal impact on the electric field generated between the discharge electrodes 170 and the reference electrode 140*b*. Similarly, changes in the relative position of the discharge electrodes 170 with respect to reference electrode 140*b*, or changes in the electric field strength generated between the discharge electrodes 170 and reference electrode 140*b* have minimal impact on the electric field generated between the spray nozzles 120 and the reference electrode 140*b***.

Preferably, reference electrodes **140*b* and 140*c* and discharge electrodes 170 are positioned such that the electric field intensity is largest between spray ends 142*b* and 142*c* and discharge tips 172. This relative position of discharge electrodes 170 and reference electrodes 140*b* and 140*c* minimizes the quantity of ionized air molecules that flow to the reference electrodes 140*b* and 140*c*.Thus, this configuration maximizes the number of ionized air molecules (corona wind) available to discharge the aerosol. Additionally, this configuration also tends to maximize the aerosol quantity that moves with the corona wind. Preferably, reference electrodes 140*b* and 140*c* are also positioned symmetrically to discharge electrodes 170. This geometric symmetry promotes symmetry in the electric field at discharge tips 172** which tends to promote ionized air flow across the plane intersecting the discharge electrodes.

A DC voltage source (see FIG. 1) electrically connects spray nozzles 120 to reference electrodes **140*a* and 140*b* and maintains spray nozzles 120 at a negative potential. A second DC voltage source (see FIG. 1) electrically connects discharge electrodes 170 to reference electrodes 140*b* and 140*c* and maintains discharge electrodes 170** at a positive potential.

A positive potential is preferred on the discharge electrodes 170 to form the corona wind discussed above. A negative voltage on the discharge electrodes 170 would form an ion stream easier; however, as described above these negative ions (electrons) have a very low momentum. Thus, using electrons to discharge the aerosol has relatively little impact on the movement of the aerosol as compared with the effect of positive ions. However, as stated above, in some applications it may actually be useful to have a negative charge on the discharge electrode, though it is not preferred in the drug delivery application.

The positive voltage on the discharge electrodes 170 strips an electron from an air molecule leaving the air molecule with a positive charge. Subsequently, the ionized air molecule will move away from the discharge electrodes 170. Additionally, the ionized air molecules are attracted to the negative charge on the aerosol. In the embodiments where the reference electrode **140*b* does not cross line LOS (see FIG. 1), the ionized air molecule will also be attracted to the negative voltage on the spray nozzles 120. Due to the closer proximity of the aerosol most, if not all, of the ionized air interacts with the aerosol. The addition of lower reference electrode 140*c* and the resulting impact on the electric field or discharge tips 172 provide a symmetry to the ionizing field. Thus, the predominate motion direction of the ionized air molecules is directly away from the discharge electrodes 170 and along the direction that the discharge electrodes 170 are pointing. Consequently, the aerosol also moves in the direction that the discharge electrode is pointing. Preferably, this direction is generally toward the device exit which, in the drug delivery application is toward the mouth of the user. In any event, the motion direction of the aerosol is principally controlled by the position/orientation of the discharge electrodes 170**.

In some applications, it may be useful to begin the corona discharge and the corona wind just prior to production of aerosol. This may assist in more completely moving the aerosol droplets away from the spray nozzle. Typically, when the voltage to the discharge electrode and the spray nozzle are applied at the same time, the positive corona begins prior to the aerosolization of the fluid because the electron stripping process is more rapid than the EHD droplet formation process. However, at times, it is useful to apply the voltage to the discharge electrode just prior to applying the voltage to the spray nozzle.

When the spray nozzles are arranged in an array, it may be necessary to add spray electrodes to the array to balance and/or shape the electric fields experienced by the other spray nozzles. A spray electrode may be a spray nozzle that is plugged, blocked, or not provided with fluid. Alternatively, the spray electrode may be shaped similarly to a discharge electrode. Additionally, spray nozzle spacing may serve a similar function.

When using a linear array as shown in FIGS. 4–6 for sprayer 100, spray electrodes 180 are placed at each end of the linear array. These spray electrodes 180 tend to balance and/or even out the electric field without having to adjust the voltages on individual spray nozzles 120, so that the adjacent spray nozzle 124 is subject to a similar electric field as the other spray nozzles 120. With each spray nozzle 120 subject to similar electric fields, each Taylor cone will then behave in a predictable manner. Consequently, the aerosol droplet size and size distribution can be predicted and controlled.

Spray nozzles 120 may be joined to manifold 190 that is supported by housing 110. Manifold 190, if employed, provides a fluid connection between a fluid source (not shown) and each spray nozzle 120. Additionally, manifold 190 interconnects each spray nozzle 120. Thus, each spray nozzle should experience approximately the same fluid pressure and each spray nozzle should experience similar fluid flow rates. Similar fluid flow rates also promote similar Taylor cone behavior. Consequently, the aerosol droplet size and size distribution can be predicted and controlled.

Manifold 190, if manufactured from a conducting material, can also electrically connect the voltage source to each spray nozzle 120 and to each spray electrode 180 installed. Due to the relatively large size of manifold 190 as compared to a spray nozzle 120 onto spray electrode 180, the voltage provided to each spray nozzle 120 or each spray electrode 180 should be similar. Consequently, the Taylor cone behavior can be predicted with greater certainty.

We have disclosed the preferred EHD apparatus and method in detail. As described earlier, the invention is also useful for delivery of many other aerosol products (e.g. fragrances, lubricants, etc). In these other uses it may be useful to move an uncharged aerosol. In this case, the discharge electrode described herein may more accurately be termed an "ionization electrode" because the ions do not discharge the charge on the aerosol, but merely provide the momentum to the corona wind to direct the flow in the desired direction. This corona wind could either be a positive or negative ion stream. Apparatus according to the invention would include aerosol source, an ionization electrode for developing the corona wind along a desired path, a reference electrode and a voltage source.

In summary, numerous benefits have been described which result from employing the concepts of the invention. The foregoing description of the invention's preferred embodiment has been presented for purposes of illustration and description. It is not intended to be exhaustive or to limit the invention to the precise form disclosed. Obvious modifications or variations are possible in light of the above teachings. These embodiments were chosen and described to best illustrate the principles of the invention and its practical application, to thereby enable one of ordinary skill in the art to best utilize the invention in various embodiments and with various modifications, as are suited to the particular use contemplated. It is intended that the scope of the invention be defined by the claims appended hereto.

We claim:

1. A directionally controlled electrohydrodynamic aerosol sprayer comprising:

a spray nozzle in fluid communication with a source of fluid to be aerosolized, the spray nozzle having at least one spray tip near which the fluid exits the spray nozzle and is aerosolized;

a discharge electrode;

a reference electrode located between the spray nozzle and the discharge electrode and crossing a line connecting the spray tip and the discharge electrode;

a first voltage source maintaining the spray nozzle at a negative or positive potential relative to the potential of the reference electrode; and a second voltage source maintaining the discharge electrode at the opposite potential relative to the potential of the reference electrode than is the spray nozzle.

2. The directionally controlled electrohydrodynamic aerosol sprayer of claim 1, wherein the reference electrode is positioned relative to the spray nozzle such that the electric field generated between the spray nozzle and the reference electrode is the highest between a spray tip of the spray nozzle and a spray end of the reference electrode, whereby the electric field minimizes the wetting of the exterior of the nozzle.

3. The directionally controlled electrohydrodynamic aerosol sprayer of claim 1, wherein the reference electrode is positioned relative to the discharge electrode, such that the electric field generated between the discharge electrode and the reference electrode is the highest between a discharge tip of the discharge electrode, and a spray end of the reference electrode.

4. A directionally controlled electrohydrodynamic aerosol sprayer comprising:

a spray nozzle in fluid communication with a source of fluid to be aerosolized, the spray nozzle having at least one spray tip near which the fluid exits the spray nozzle and is aerosolized generally along a selected aerosol spray path;

a discharge electrode for producing ions near an ionization site on the discharge electrode and a corona wind from the discharge electrode along a desired path, wherein the discharge electrode is oriented such that the desired path makes an angle of less than 90 degrees to the selected aerosol spray path;

a reference electrode located between the spray nozzle and the discharge electrode;

a first voltage source maintaining the spray nozzle at a negative or positive potential relative to the potential of the reference electrode; and a second voltage source maintaining the discharge electrode at the opposite potential relative to the potential of the reference electrode than is the spray nozzle.

5. A directionally controlled electrohydrodynamic aerosol sprayer comprising:

a sprayer housing having an exit for communicating the aerosol to a user;

a spray nozzle within the housing and in fluid communication with a source of fluid to be aerosolized;

a discharge electrode capable of producing a positive ion stream from air molecules proximate the discharge electrode and oriented such that the positive ion stream may intercept the aerosol from the spray nozzle and move at least a portion of the aerosol generally in a direction toward the exit;

a first reference electrode located between the spray nozzle and the discharge electrode;

a first voltage source maintaining the spray nozzle at a negative potential relative to the potential of the reference electrode; and a second voltage source maintaining the discharge electrode at a positive potential relative to the potential of the reference electrode.

6. The directionally controlled electrohydrodynamic aerosol sprayer of claim 5, wherein the spray nozzle has at least one spray tip near which the fluid exits the spray nozzle and is aerosolized and the first reference electrode is located between the spray nozzle and the discharge electrode and crossing a line connecting the spray tip and the discharge electrode.

7. The directionally controlled electrohydrodynamic aerosol sprayer of claim 5 wherein the discharge electrode has a configuration and an orientation to produce a positive ion stream which intercepts the aerosol along an aerosol path downstream of the spray nozzle to discharge the aerosol and to move at least a portion of the aerosol generally in a direction substantially parallel to the positive ion stream.

8. The directionally controlled electrohydrodynamic aerosol sprayer of claim 5, wherein the spray nozzle is positioned to dispense the aerosol generally along a path parallel to a selected aerosol spray direction and the discharge electrode is positioned such that the positive ion stream may intercept the aerosol spray direction at an angle of between about 0 and 120 degrees.

9. The directionally controlled electrohydrodynamic aerosol sprayer of claim 8, wherein the spray nozzle and the discharge electrode are positioned such that the positive ion stream may intercept the aerosol spray direction at an angle of between about 30 and 90 degrees.

10. The directionally controlled electrohydrodynamic aerosol sprayer of claim 5, which further comprises:

a second reference electrode located such that the discharge electrode is located between the first reference electrode and the second reference electrode and wherein the second reference electrode is at a potential which is positive with respect to the spray nozzle and negative with respect to the discharge electrode.

11. The directionally controlled electrohydrodynamic aerosol sprayer of claim 10, wherein the second reference electrode is positioned such that a line drawn from the spray nozzle to the discharge electrode passes through the second reference electrode.

12. The directionally controlled electrohydrodynamic aerosol sprayer of claim 10, which further comprises:

a third reference electrode located such that the spray nozzle is located between the first reference electrode and the third reference electrode and wherein the third reference electrode is at a potential which is positive with respect to the spray nozzle and negative with respect to the discharge electrode.

13. The directionally controlled electrohydrodynamic aerosol sprayer of claim 12, wherein the third reference electrode is positioned such that a line drawn from an end of the second reference electrode nearest the spray nozzle to an end of the third reference electrode nearest the spray nozzle does not pass through the spray nozzle.

14. A directionally controlled electrohydrodynamic aerosol sprayer comprising:

a sprayer housing having an exit for communicating aerosol to a user;

a plurality of spray nozzles within the housing and in fluid communication with a source of fluid to be aerosolized;

a plurality of discharge electrodes capable of producing positive ion streams from air molecules proximate the discharge electrodes and oriented such that the positive ion streams may intercept the aerosol from the spray nozzles and move at least a portion of the aerosol generally in a direction toward the exit;

at least one reference electrode located between the spray nozzles and the discharge electrodes;

a first voltage source maintaining the spray nozzles at a negative potential relative to the potential of the at least one reference electrode; and a second voltage source maintaining the discharge electrodes at a positive potential relative to the potential of the at least one reference electrode.

15. The directionally controlled electrohydrodynamic aerosol sprayer of claim 14, wherein the at least one reference electrode crosses a line connecting the spray nozzles and the discharge electrodes, whereby the electric field created between the reference electrode and the spray nozzles is substantially de-coupled from the electric field created between the discharge electrodes and the at least one reference electrode.

16. The directionally controlled electrohydrodynamic aerosol sprayer of claim 14 wherein the discharge electrodes have a configuration and an orientation to produce a positive ion stream which intercepts the aerosol along an aerosol path downstream of the spray nozzles to discharge the aerosol and to move at least a portion of the aerosol generally in a direction substantially parallel to the positive ion stream.

17. The directionally controlled electrohydrodynamic aerosol sprayer of claim 14, wherein the spray nozzles are positioned to dispense the aerosol generally along a path parallel to a selected aerosol spray direction and the discharge electrodes are positioned such that the positive ion stream may intercept the aerosol spray direction at an angle of between about 0 and 120 degrees.

18. The directionally controlled electrohydrodynamic aerosol sprayer of claim 17, wherein the spray nozzles and the discharge electrodes are positioned such that the positive ion stream may intercept the aerosol spray direction at an angle of between about 30 and 90 degrees.

19. Device for delivering electrically neutral aerosol droplets substantially along a desired path comprising:

means for converting a fluid into aerosol droplets having a negative electrical charge with respect to a reference potential; and discharge electrode means for producing ions positively charged with respect to the reference potential and a corona wind from the discharge electrode means in a direction along the desired path for intercepting the aerosol droplets and moving the droplets in the direction along the desired path away from the means for converting a fluid.

20. The device of claim 19 for delivering electrically neutral aerosol droplets substantially along a desired path further comprising a field modifying element located between the means for converting a fluid and the means for producing ions and comprising either a dielectric means or a reference electrode means at the reference potential.

21. A device for delivering electrically neutral aerosol droplets to a user comprising:

housing means including an exit communicating with the user;

electrohydrodynamic means for converting a fluid into aerosol droplets having a negative electrical charge; and discharge electrode means for producing positively charged ions and a corona wind from the discharge electrode means in a direction intercepting the aerosol droplets and generally toward the exit.

22. The device of claim 21 for delivering electrically neutral aerosol droplets to a user further comprising first reference electrode means at the reference potential located between the electrohydrodynamic means and the discharge electrode means.

23. The device of claim 22 for delivering electrically neutral aerosol droplets to a user further comprising:

second reference electrode means located such that the discharge electrode means is between the first reference electrode means and the second reference electrode means, and third reference electrode means located such that the electrohydrodynamic means is located between the first reference electrode means and the third reference electrode means, and wherein the first, second and third reference electrode means are each at a potential which is positive with respect to the electrohydrodynamic means and negative with respect to the discharge electrode means.

24. Apparatus for delivering therapeutic aerosol droplets substantially along a desired path by EHD spraying comprising:

a EHD spray nozzle in communication with a source of therapeutic fluid to be aerosolized, the EHD spray nozzle having a spray tip and a central axis;

a discharge electrode having a sharp point or edge near an end thereof and a central axis, the discharge electrode being positioned and oriented with respect to the spray nozzle such that the spray tip and the sharp point or edge are proximate and such that the angle between the axis of the spray nozzle and the axis of the discharge electrode is between about 0 and 120 degrees;

a reference electrode at a reference potential located between the EHD spray nozzle and the discharge electrode;

first voltage source maintaining the EHD spray nozzle at a negative potential with respect to the reference potential; and second voltage source maintaining the discharge electrode at a positive potential with respect to the reference potential.

25. The method of claim 24 for delivering therapeutic aerosol droplets substantially along a desired path by EHD spraying wherein the angle between the spray nozzle central axis and the discharge electrode central axis is between about 30 and 90 degrees.

26. A method for delivering aerosol droplets substantially along a desired path comprising:

providing an aerosol source and a discharge electrode;

providing a reference potential on a reference electrode located between the aerosol source and the discharge electrode;

producing aerosol droplets near the aerosol source, the aerosol droplets being charged with respect to the reference potential;

producing ions near an ionization site on a discharge electrode and a corona wind from the ionization site in a direction along the desired path, the ions having a charge that is opposite to the charge of the aerosol droplets; and intercepting the aerosol droplets with the corona wind such that the aerosol droplets are electrically discharged and are moved along with the corona wind in the desired path.

27. The method of claim 26 for delivering aerosol droplets substantially along a desired path which further includes producing the aerosol droplets by electrohydrodynamic spraying.

28. The method of claim 26 for delivering aerosol droplets substantially along a desired path which further includes positioning and orienting the discharge electrode such that the corona wind moves in a direction away from the discharge electrode and away from the aerosol source.

29. The method of claim 26 for delivering aerosol droplets substantially along a desired path which further includes:

producing an aerosol stream from the aerosol droplets from the tip of a spray nozzle, the aerosol stream moving away from the aerosol source in a direction substantially parallel to the spray nozzle central axis; and orienting the discharge electrode such that the corona wind intercepts the aerosol source central axis at an angle of between about 0 and 120 degrees.

30. The method of claim 26 for delivering aerosol droplets substantially along a desired path which further includes:

producing the aerosol droplets by electrohydrodynamic spraying;

producing an aerosol stream from the aerosol droplets near the tip of a spray nozzle, the aerosol stream moving away from the tip of the spray nozzle in a direction substantially parallel to the spray nozzle central axis;

orienting the discharge electrode such that the corona wind intercepts the aerosol source central axis at an angle of between about 0 and 120 degrees; and positioning the reference electrode such that the end of the reference electrode substantially abuts the line of sight between the tip of the spray nozzle and the ionization site of the discharge electrode.

31. A method for delivering therapeutic aerosol droplets substantially along a desired path by EHD spraying comprising:

providing an EHD spray nozzle having a central axis;

providing a discharge electrode having a sharp point or edge;

providing a reference potential on a reference electrode located between the EHD spray nozzle and the discharge electrode;

producing aerosol droplets near the tip of the EHD spray nozzle, the aerosol droplets being negatively charged with respect to the reference potential;

producing ions near the sharp point or edge of the discharge electrode and a movement of ions away from the discharge electrode in a direction along the desired path, the ions being positively charged with respect to the reference potential; and intercepting the aerosol droplets with the ions downstream of the tip of the spray nozzle and downstream of the sharp point or edge such that the aerosol droplets are electrically discharged and are moved along with the ions in the desired path.

32. The method of claim 31 for delivering therapeutic aerosol droplets substantially along a desired path by EHD spraying which further comprises orienting the discharge electrode such that the angle between the spray nozzle central axis and direction of movement of ions away from the discharge electrode is between about 0 and 120 degrees.

33. The method of claim 31 for delivering therapeutic aerosol droplets substantially along a desired path by EHD spraying which further comprises orienting the discharge electrode such that the angle between the spray nozzle central axis and direction of movement of ions away from the discharge electrode is between about 30 and 90 degrees.

34. Device for delivering aerosol substantially along a desired path comprising:

at least one aerosol source; and at least one ionization electrode for producing a stream of ions therefrom in a direction along the desired path for intercepting and moving the aerosol in the direction along the desired path away from the aerosol source.

35. The device of claim 34 wherein the aerosol source is capable of delivering an aerosol with a positive charge, a negative charge or with substantially no charge with respect to ground.

36. The device of claim 35 which further comprises:

at least one dielectric device between the aerosol source and the ionization electrode.

37. The device of claim 35 which further comprises:

a reference electrode located between the aerosol source and the ionization electrode;

a first voltage source maintaining the aerosol source at a negative potential relative to the potential of the reference electrode; and a second voltage source maintaining the ionization electrode at a positive potential relative to the potential of the reference electrode.

38. A method for delivering aerosol droplets substantially along a desired path comprising:

providing an aerosol source and an ionization electrode;

producing aerosol droplets near the aerosol source;

producing ions near an ionization site on the ionization electrode and a corona wind therefrom in a direction along the desired path; and intercepting the aerosol droplets with the corona wind such that the aerosol droplets are moved along with the corona wind in the desired path.

39. The method for delivering aerosol droplets substantially along a desired path according to claim 38 and further comprising:

providing a reference potential on a reference electrode located between the aerosol source and the discharge electrode;

providing an electrical charge on the aerosol droplets; and providing an electrical charge on the ionization electrode that is opposite to the charge on the aerosol droplets.

* * * * *